United States Patent [19]
Ogiso et al.

[11] Patent Number: 5,880,100
[45] Date of Patent: Mar. 9, 1999

[54] METHOD FOR INHIBITING BINDING OF HUMAN LENS CELLS

[75] Inventors: Manabu Ogiso, Kanagawa; Chikako Noro, Ibaraki, both of Japan

[73] Assignee: Research Development Corporation of Japan, Saitama, Japan

[21] Appl. No.: 703,874

[22] Filed: Aug. 27, 1996

[51] Int. Cl.$^6$ .............................. A61K 31/70; C07H 15/00
[52] U.S. Cl. ................................. 514/25; 514/54; 514/61; 514/62; 536/17.2; 536/18.7; 536/53; 536/55; 536/55.1; 536/55.2
[58] Field of Search .................................. 514/25, 54, 61, 514/62; 536/17.2, 18.7, 53, 55, 55.1, 55.2

[56] References Cited

FOREIGN PATENT DOCUMENTS 1006598  10/1994  Belgium .
94/13275  6/1994  WIPO .

*Primary Examiner*—Kathleen K. Fonda
*Attorney, Agent, or Firm*—Wenderoth, Lind & Ponack, L.L.P.

[57] ABSTRACT

The present invention provide a method of inhibiting an irregular binding of human cells caused by specific adhesion of Lewis$^x$ glycolipids by administering any of an oligosaccharide having a Lewis$^x$ sugar chain structure, CMP-sialic acid, and a sialidase inhibitor, into the lens, and an inhibitory agent for this purpose. This make it possible to prevent or improve cataract of the lens caused by aging.

2 Claims, 6 Drawing Sheets

METHOD FOR INHIBITING BINDING OF HUMAN LENS CELLS

FIELD OF THE INVENTION

The present invention relates to a method for inhibiting an irregular binding of human lens cells caused by specific adhesion of Lewis$^x$ glycolipids. More specifically, the present invention relates to a novel method for effectively inhibiting the irregular binding of lens cells which is a cause of human senile cataract, and an inhibitory agent for the irregular cell binding.

DESCRIPTION OF RELATED ART

Cataract is a disease in which the lens within the eyeball becomes opaque, whereby the visual acuity is seriously impaired, and finally causes loss of eyesight. Cataract may be caused congenitally or be acquired. Known types of acquired cataract include senile, diabetic, traumatic and those caused by irradiation such as of ultraviolet or X-rays.

Since the recent improvement of life environments, nutritional conditions and the perfection of medical systems bring about progress of life expectancy, senile cataract has become one of the typical senile diseases in many middle and aged patients of more than fifty years of age.

The conventional practice of cataract therapy is lens extirpation technique, in which cataractous lens is surgically removed from the eyeball. It is now possible to easily recover the visual acuity after lens extirpation by inserting an intraocular lens. In an ordinary lens extirpation, however, it is impossible to remove all lens cells from the eyeball, and some of the epithelial cells remain in the lens. There are therefore such problems as occurrence of so-called after the cataract caused by these residual cells after operation. In addition, the risk leads to a more serious disease such as uveitis or secondary glaucoma.

While the lens extirpating operation is not always the best cataract therapy as described above, such a surgical operation is at present the only method to recover the visual acuity impaired by cataract or avoid the risk of losing eyesight. A method of clearing a cataractous lens by administering a drug has not as yet been developed.

Development of an effective drug for prevention or therapy of cataract has not been successful mainly because the mechanism causing cataractous lens has not been clarified. More specifically, it is known that the lens is not governed by blood vessels or nerves unlike the other somatic cells and that soluble proteins known as crystallins and a lamella structure of cells keep lens transparent. Important features of the lens are that lens epithelial cells migrate into the lens nucleus to be accumulated during a person's life, and that most of the cells have lost their nuclei. It is therefore difficult to conceive that, in spontaneous occurrence of a cataractous lens as in senile cataract, the cause should be expression of specific genes or degeneration of cells themselves, and this makes it difficult to develop a drug through ordinary techniques.

The present inventors have assumed that the binding state of lens cells changes with aging and this is a trigger of senile cataract. The inventors carried out studies on glycolipid existing on cell membrane to clarify its role and changes, and have reported the following fact.

That is, glycolipid of a human lens include neolacto, globo, and ganglio-series ones, and further, there are available Lewis$^x$ glycolipid and sialyl-Lewis$^x$ glycolipid known as cancer markers of somatic cells [Ogiso, M. et al (1992) J. Biol. Chem., 267, p. 6467–6470; Ogiso, M. et al (1993) J. Biol. Chem., 268, p. 13242–13247; Ogiso, M. (1993) Glycopathology, 299–304, Kodansha Scientific; Ariga, T. et al (1994) J. Biol. Chem., 269, p. 2667– 2675; Ogiso, M. et al (1995) Biochim. Biophys. Acta, 1256, p. 166–174]. A protein known as selectin, which binds specifically to sialyl-Lewis$^x$ glycolipid in the presence of $Ca^{2+}$, is present in the membrane of the lens cells (Ogiso, M. et al, non-published). Binding of this selectin and sialyl-Lewis$^x$ glycolipid forms regular combination of lens cells, maintaining transparency of the lens (see FIG. 1).

In human senile cataract, on the other hand, the content of ganglioside which is an acidic glycolipid increases with aging and the progress of cataract [Ogiso, M. et al (1990) Invest. Ophthalmol. Vis. Sci., 31, 2171–2179]. There is Lewis$^x$ antigen in neutral glycolipid, and the content thereof increases similarly with aging and the progress of cataract [Ogiso, M. et al (1992) J. Biol. Chem., 267, p. 6467–6470]. However, the increase in the ganglioside content is dependent on ganglio-series glycolipid, and the increase in the content of sialyl-Lewis$^x$ glycolipid brings about no marked change [Ogiso, M. et al (1995) Exp. Eye. Res., 60, p. 317–323]. Increase in the amount of Lewis$^x$ glycolipid with aging is therefore considered to result from removal of sialic acid from sialyl-Lewis$^x$ glycolipid showing only a little change. More specifically, this terminal sialic acid is connected with galactose of the Lewis$^x$ terminal, and ionized $COO^-$ is present near the position of this connection. Binding of sialyl-Lewis$^x$ glycolipid and selectin as described above is also considered to be reinforced by $Ca^{2+}$ ions via this $COO^-$. However, because this ionized $COO^-$ is rather unstable in an aqueous solution, it is highly probable that removal of sialic acid occurs at this position in the absence of connection with selectine. Because of the absence of electric charge, Lewis$^x$ glycolipid is considered to be relatively stable.

In a normal human lens, as described above, sialyl-Lewis$^x$ glycolipid and selectin present on the surface of cells specifically bind to each other. With the progress of aging, sialic acid is removed from sialyl-Lewis$^x$ glycolipid and is transformed into Lewis$^x$ glycolipid. The Lewis$^x$ glycolipid is known to specifically combine with Lewis$^x$ glycolipid on neighboring cell surfaces (see FIG. 2). This specific adhesion of Lewis$^x$ glycolipids causes disturbance of regularity of lens cells'bindings, and this in turn exerts an effect on ion transport and transduction on the cell membrane, thus forming the primary cause of a cataractous lens, resulting in protein agglutination.

Furthermore, the present inventors clarified that the relationship between a cataractous lens and glycolipid as described above is specific to humans and monkeys (primate). More specifically, as a result of detection of expression of Lewis$^x$ glycolipid and sialyl-Lewis$^x$ glycolipid from lenses of many mammals, expression of sialyl-Lewis$^x$ glycolipid was observed in many mammals including rat, pig and primates, whereas it has been confirmed that expression of Lewis$^x$ glycolipid in the lens is limited to primates [Ogiso, M. et al (1994), Exp. Eye. Res., 59, p. 653–664]. In fact, in a galactosemic cataract rat or an inherited cataract-suffering mouse, commonly used as cataract-model animals, not only is there no increase of Lewis$^x$ glycolipids with the progress of cataract, but also synthesis of Lewis$^x$ glycolipid does not intrinsically occur [Ogiso, M. et al (1995)], Exp. Eye. Res., 60, p. 317–323]. These findings suggest that it is highly probable that human cataract is essentially different from that of laboratory animals, and the critical mechanism of lens cataract clarified by the use of laboratory animals will not basically agree with that of humans.

In primates, localization of Lewis$^x$ glycolipid or sialyl-Lewis$^x$ glycolipid is not detected in external epithelial cells, but in fiber cells in the lens [Ogiso, M. et al (1994), Glycobiology, 4, p. 375–382; Ogiso, M. et al (1995), Exp. Eye. Res., 60, p. 317–323]. This is confirmed by immunohistchemical identification of Lewis$^x$ glycolipid or sialyl-Lewis$^x$ glycolipid in a simian lens cells (a photograph is given in FIG. 3), and from the fact that Lewis$^x$ glycolipid (Le$^x$) and sialyl-Lewis$^x$ glycolipid (sialyl-Le$^x$) were detected in the same fiber cell region in the lens.

SUMMARY OF THE INVENTION

As described above, the present inventors clarified the cause of human lens cataract from quite a new standpoint of binding of Lewis$^x$ glycolipids existing on the cell surfaces. The present invention has therefore an object to provide, on the basis of these new findings, a novel method for treating cataract by administration of an agent.

The present invention provides a method of inhibiting an irregular binding of human lens cells caused by specific adhesion of Lewis$^x$ glycolipids, which method comprises administering an oligosaccharide having a sugar chain structure similar to that of Lewis$^x$ glycolipid into the lens to bind this oligosaccharide with Lewis$^x$ glycolipid, thereby preventing the specific adhesion of Lewis$^x$ glycolipids.

The present invention provides another method of inhibiting an irregular binding of human lens cells caused by specific adhesion of Lewis$^x$ glycolipids, which method comprises administering CMP-sialic acid into the lens to synthesize sialyl-Lewis$^x$ glycolipid from Lewis$^x$ glycolipid, thereby preventing the specific adhesion of Lewis$^x$ glycolipids.

The present invention further provides a method of inhibiting an irregular binding of human lens cells caused by specific adhesion of Lewis$^x$ glycolipids, which method comprises administering an inhibitor of sialidase, a sialic acid lyase, to inhibit degradation of sialyl-Lewis$^x$ glycolipids into Lewis$^x$ glycolipids, thereby preventing the specific adhesion of Lewis$^x$ glycolipids.

In addition, the present invention provides an inhibitory agent for the irregular binding of hummans lens cells which contains any of oligosaccharide having a sugar chain structure of Lewis$^x$ glycolipids, CMP-sialic acid, and a sialidase inhibitor as an effective ingredient.

DETAILED DESCRIPTION OF THE INVENTION

Figure 1:
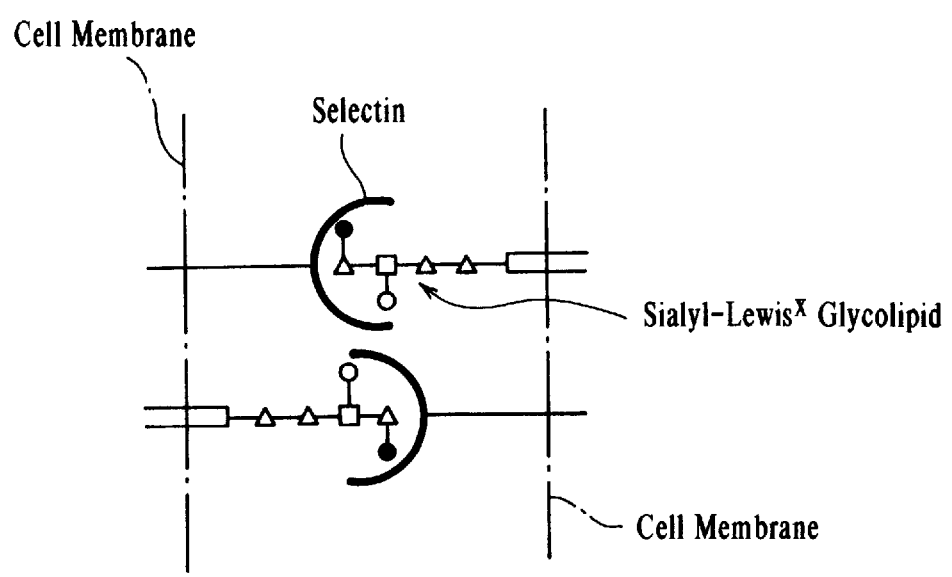
FIG. 1 is a schematic view illustrating a state of binding of normal lens cells and FIG. 2 is a schematic view illustrating a state of binding of catractous lens cells.

The method and the drug of the present invention were developed on the basis of the following relationship between lens cells and glycolipid as found by the present inventors:

(1) In a normal lens, sialyl-Lewis$^x$ glycolipid and selectin present on the fiber cell surface specifically bind each other, and this maintains regular binding of the lens cells, making lens transparent (see FIG. 1).

(2) Along with aging, sialic acid of sialyl-Lewis$^x$ glycolipids leaves, thus causing an increase in Lewis$^x$ glycolipids.

Figure 2:
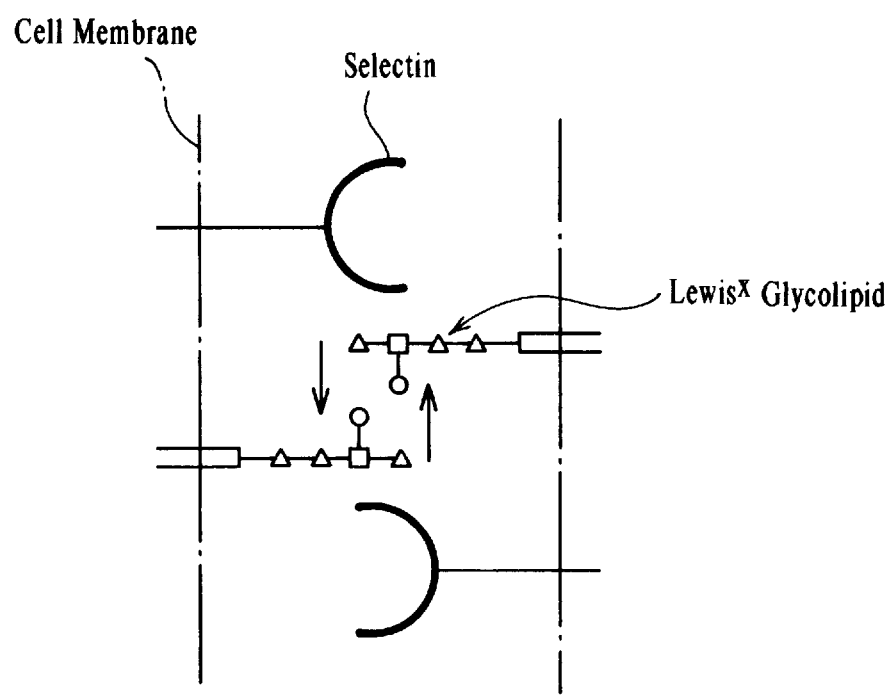
Figure 3A:
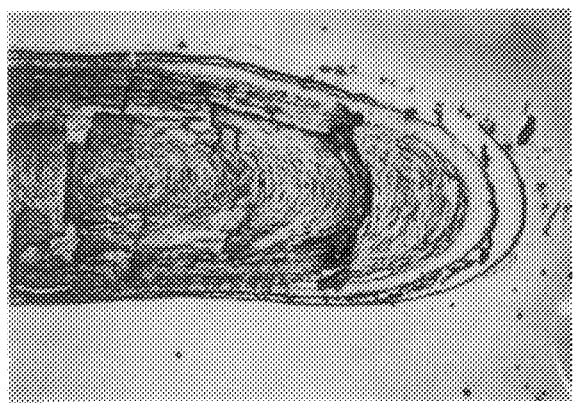
FIG. 3 is a photomicrograph of simian lens fiber cells showing the same localization of Lewis$^x$ glycolipid and sialyl-Lewis$^x$ glycolipid.
Figure 3B:
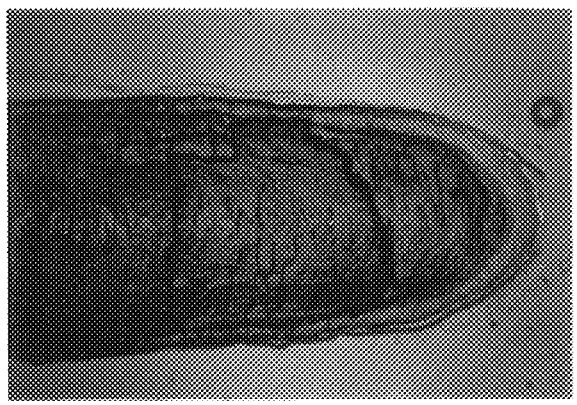
Figure 3C:
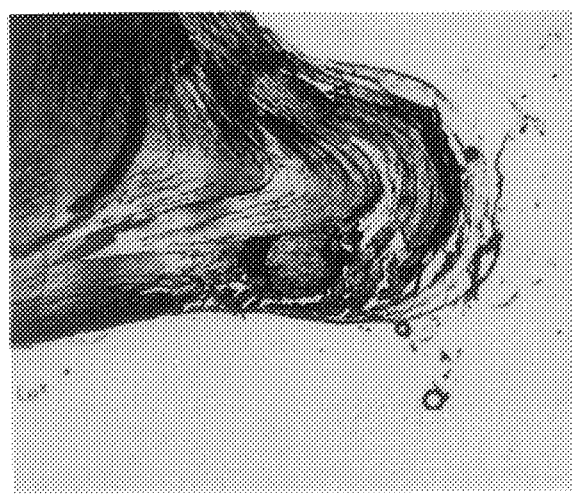
Figure 3D:
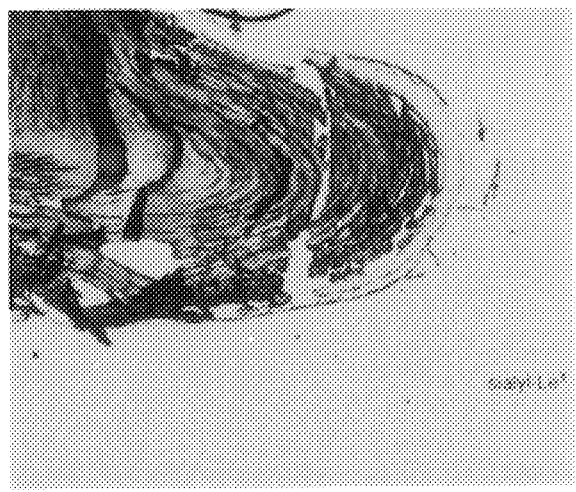

(3) Specific adhesion of Lewis$^x$ glycolipids (see FIG. 2) results in an increased irregular binding between lens cells, which in turn causes cataract of the lens.

The basic principle of the method of the present invention is therefore to prevent the specific adhesion of Lewis$^x$ glycolipids as described in (3) above, and one of the concrete means to achieve this is to administer oligosaccharide having a glycolipid sugar chain structure of Lewis$^x$ glycolipid to the lens. More particularly, oligosaccharide as described above specifically binds to Lewis$^x$ glycolipid because of the affinity thereof with the glycolipid, thus effectively blocking the connection between Lewis$^x$ glycolipids.

The increase in Lewis$^x$ glycolipids caused by aging is due to elimination of sialic acid from sialyl-Lewis$^x$ glycolipids as described in (2) above. It is therefore effective to administer an inhibitor of an enzyme acting on this elimination of sialic acid, i.e., sialidase. This prevents degradation of sialyl-Lewis$^x$ glycolipid into Lewis$^x$ glycolipid, thus preventing the specific adhesion of Lewis$^x$ glycolipids and hence improving cataract of the lens.

Figure 4:
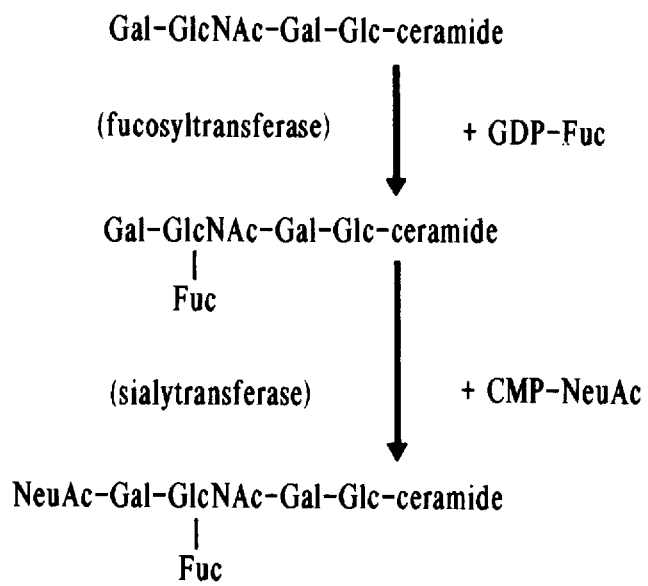
FIG. 4 illustrates a biosynthesis pathway from Lewis$^x$ glycolipid to sialyl-Lewis$^x$ glycolipid.
Figure 5:
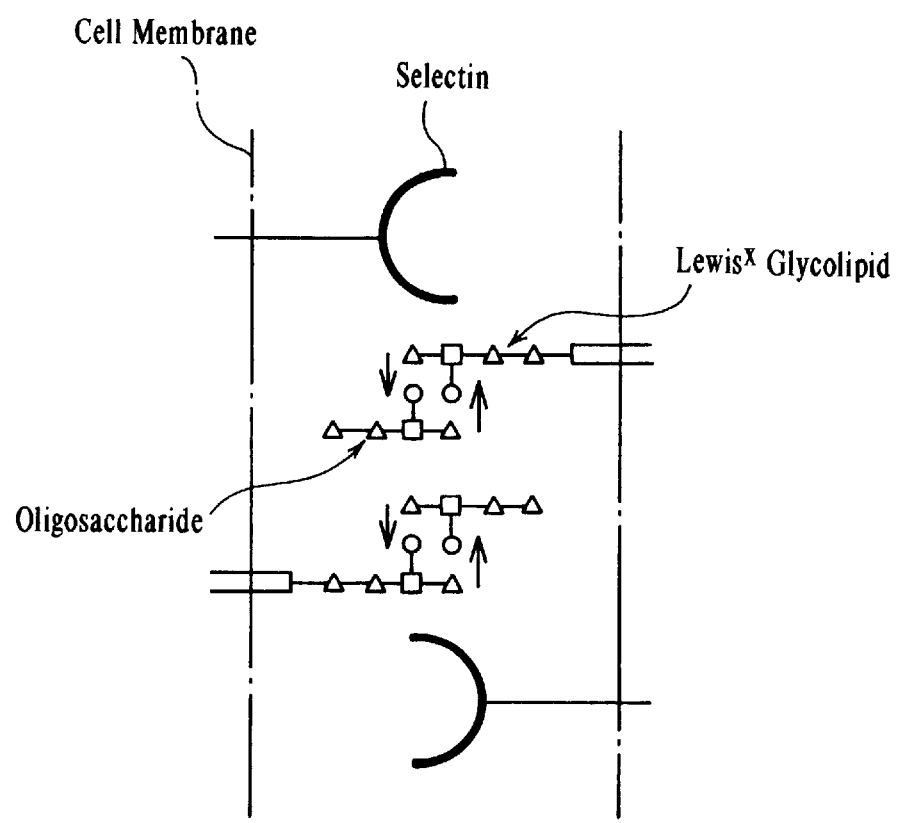
FIG. 5 is a schematic view illustrating a state of prevention of binding of Lewis$^x$ glycolipid with oligosaccharide.

Furthermore, the present inventors found, through an enzymatic reaction as shown in FIG. 4, the possibility of synthesis of sialyl-Lewis$^x$ glycolipid from Lewis$^x$ glycolipid. Accordingly, by administering CMP-sialic acid participating in this synthesis, it is possible to reconvert Lewis$^x$ glycolipids, which have increased with aging, into sialyl-Lewis$^x$ glycolipids. It is highly probable that sialyl-Lewis$^x$ glycolipids responsible for regular cell binding in lens cells are synthesized from Lewis$^x$ glycolipids actually through a reaction as shown in FIG. 4. In other words, the increase of Lewis$^x$ glycolipids by aging, partly caused by (2) above, may be attributable to interruption of conversion from Lewis$^x$ glycolipids to sialyl-Lewis$^x$ glycolipids. Administration of CMP-sialic acid is therefore an effective means to enhance biosynthesis of sialyl-Lewis$^x$ glycolipids.

DESCRIPTION OF PREFERRED EMBODIMENTS

Figure 6:
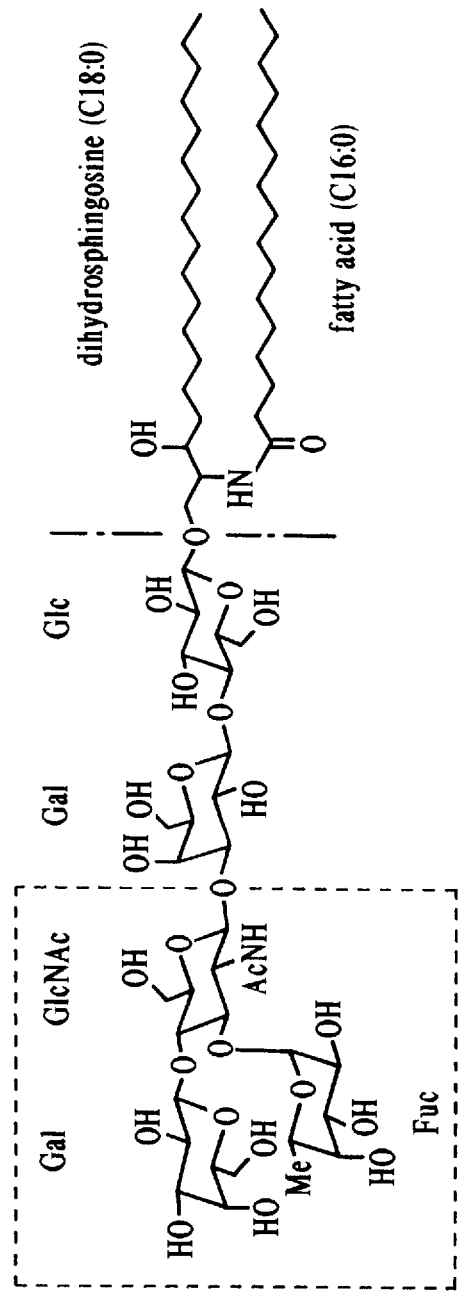
FIG. 6 is a chemical formula illustrating the structure of Lewis$^x$ glycolipid.

Oligosaccharide used in the present invention is a sugar chain having a structure identical with, or similar to, that of the sugar chain portion of Lewis$^x$ glycolipid. In the structure shown in FIG. 6 of Lewis$^x$ glycolipid, at least the trisaccharide portion (within the broken line in FIG. 6) at the terminal thereof can be used as a separated oligosaccharide. As such oligosaccharide, products and synthetic materials separated or extracted from human or cow's milk are commercially available, and can be employed for this purpose. For example, these products include lacto-N-fucopentaose (LNFP III: made by Seikagaku Kogyo Company) and 3-fucosyllactose (3-FL: made by Seikagaku Kogyo Company) as oligosaccharide extracted from human milk, and Lewis x-type trisaccharide (made by Seikagaku Kogyo Company) as a synthetic oligosaccharide.

CMP-sialic acid used in the present invention is a product of, for example, connection of CMP (cytidine monophosphate) to sialic acid such as N-acetylneuraminic acid or N-glycolylneuraminic acid. It may be prepared by a conventional method, or a commercially available product (for example, CMP-N-acetylneuraminic acid: made by Wako Jun-yaku Company) may be used.

As the sialidase inhibitor used in the present invention, for example, a commercially available product such as 2,3 dehydro 2 deoxy-N-acetylneuraminic acid (made by Sigma Company) may be employed. N-acetylneuraminic acid as described above may also be applicable. The purpose is, in the enzymatic equilibrium, to increase products, thereby increasing the reverse reaction, this making it possible to prevent an elimination of sialic acid from sialyl-Lewis$^x$ glycolipids.

The oligosaccharide, CMP-sialic acid and sialidase inhibitor can be formulated into an eye-lotion containing these as effective ingredients. The content of each such ingredient may be within a range of from about 1 to 10 mg/ml.

A typical composition of the eye-lotion (aqueous solution) containing oligosaccharide is as follows:

Boric acid: 1.60 (%)

methylcellulose: 0.50 oligosaccharide (LNFP-III):0.1 to 1.0

What is claimed is:

1. A method of inhibiting binding of human lens cells caused by adhesion of Lewis$^x$ glycolipid on a human lens cell with Lewis$^x$ glycolipid on another human lens cell, which method comprises administering CMP-sialic acid into the lens to synthesize sialyl- Lewis$^x$ glycolipid from Lewis$^x$ glycolipid, thereby preventing the adhesion of Lewis$^x$ glycolipids to each other.

2. A method of inhibiting binding of human lens cells caused by adhesion of Lewis$^x$ glycolipid on a human lens cell with Lewis$^x$ glycolipid on another human lens cell, which method comprises administering a sialidase inhibitor into the lens to inhibit degradation of sialyl-Lewis$^x$ glycolipid into Lewis$^x$ glycolipid, thereby preventing the adhesion of Lewis$^x$ glycolipids to each other.

* * * * *